United States Patent
Lai et al.

(10) Patent No.: US 11,565,268 B2
(45) Date of Patent: *Jan. 31, 2023

(54) CONVECTIVE PCR DEVICE

(71) Applicant: Credo Biomedical Pte Ltd., Singapore (SG)

(72) Inventors: Ying-Ta Lai, New Taipei (TW); Yu-Cheng Ou, New Taipei (TW); Ming-Lung Hung, New Taipei (TW); Cheng-Yueh Chung, New Taipei (TW); Han-Yi Chen, New Taipei (TW)

(73) Assignee: Credo Diagnostics Biomedical Pte. Ltd., Singapore (SG)

( * ) Notice: Subject to any disclaimer, the term of this patent is extended or adjusted under 35 U.S.C. 154(b) by 196 days.

This patent is subject to a terminal disclaimer.

(21) Appl. No.: 16/221,562

(22) Filed: Dec. 16, 2018

(65) Prior Publication Data

US 2019/0193080 A1 Jun. 27, 2019

(30) Foreign Application Priority Data

Dec. 22, 2017 (CN) .......................... 201711400272.0

(51) Int. Cl.
*B01L 7/00* (2006.01)
*C12Q 1/6851* (2018.01)
(Continued)

(52) U.S. Cl.
CPC ................ *B01L 7/52* (2013.01); *B01L 7/525* (2013.01); *B01L 7/54* (2013.01); *C12Q 1/686* (2013.01);
(Continued)

(58) Field of Classification Search
None
See application file for complete search history.

(56) References Cited

U.S. PATENT DOCUMENTS 9,404,151 B2 8/2016 Chandra
2010/0075312 A1* 3/2010 Davies ...................... B01L 7/54
435/287.2
(Continued)

FOREIGN PATENT DOCUMENTS

CN 201770704 * 3/2011
CN 201770704 U * 3/2011
(Continued)

OTHER PUBLICATIONS

Zhi-Yong Wu et al., A thermostat chip of indium tin oxide glass substrate for static polymerase chain reaction and in situ real time fluorescence monitoring, Research Center of Analytical Science, ELSEVIER, ScienceDirect, XP022473226, 2008, pp. 89-96.
(Continued)

*Primary Examiner* — Donald R Spamer
*Assistant Examiner* — Nathan G Esperon
(74) *Attorney, Agent, or Firm* — Winston Hsu

(57) ABSTRACT

The present invention discloses a convective PCR apparatus by using a transparent conductive thin film to replace the traditional metal heater. The PCR reaction is activated when the container with reagents contacted the heated transparent conductive thin film and the temperature inside the container raised to initiate the convective circulation. Also, the present invention could apply for a quantitative PCR reaction by adding a specific probe, a fluorescent dye, a light source, or a photon receiver.

14 Claims, 3 Drawing Sheets

(51) Int. Cl.
*C12Q 1/686* (2018.01)
*C12Q 1/6844* (2018.01)

(52) U.S. Cl.
CPC ......... *C12Q 1/6844* (2013.01); *C12Q 1/6851* (2013.01); *B01L 2200/025* (2013.01); *B01L 2300/0663* (2013.01); *B01L 2300/1805* (2013.01); *B01L 2300/1827* (2013.01); *B01L 2300/1844* (2013.01); *C12Q 2527/101* (2013.01); *C12Q 2527/15* (2013.01)

(56) References Cited

U.S. PATENT DOCUMENTS

| | | | |
|---|---|---|---|
| 2010/0105035 A1* | 4/2010 | Hashsham | G01N 21/645 435/6.19 |
| 2012/0244047 A1* | 9/2012 | Teng | B01L 7/04 422/562 |
| 2013/0101983 A1 | 4/2013 | Chandra | |
| 2016/0244810 A1 | 8/2016 | Su | |

FOREIGN PATENT DOCUMENTS

| | | | |
|---|---|---|---|
| CN | 102914521 A | | 2/2013 |
| CN | 103173434 | * | 6/2013 |
| CN | 103173434 A | | 6/2013 |
| CN | 103756871 | * | 4/2014 |
| CN | 103756871 A | * | 4/2014 |
| CN | 205635562 | * | 10/2016 |
| CN | 205635562 U | * | 10/2016 |
| CN | 104630056 B | | 11/2017 |
| EP | 3 360 976 A1 | | 8/2018 |
| JP | 2005-516588 A | | 6/2005 |
| JP | 2005-323519 A | | 11/2005 |
| JP | 2012-118055 A | | 6/2012 |
| JP | 2013-516975 A | | 5/2013 |
| JP | 2014-82987 A | | 5/2014 |
| JP | 2017-176177 A | | 10/2017 |
| KR | 20110088092 | * | 8/2011 |
| KR | 20110088092 A | * | 8/2011 |
| TW | 201311886 A1 | | 3/2013 |
| TW | 201333188 A1 | | 8/2013 |
| TW | 201339308 | * | 10/2013 |
| TW | 201339308 A | * | 10/2013 |
| TW | 201741450 A | | 12/2017 |
| WO | WO-2013003976 A1 * | 1/2013 | ............... B01L 7/52 |
| WO | WO-2013091472 A1 * | 6/2013 | ............... B01L 7/54 |

OTHER PUBLICATIONS

Bai-Yan Qu et al., Optimization of direct whole blood PCR amplification with applications on a static thermostat chip, Electronic supplementary material, Springer, Sep. 12, 2007, XP019559819, pp. 1499-1504.

Hsiao-Fen Grace Chang et al., A thermally baffled device for highly stabilized convective PCR, Biotechnology Journal, Technical Report, pp. 662-666, Jan. 13, 2012, XP055526081.

Zhi-Yong Wu et al., A thermostat chip of indium tin oxide glass substrate for static polymerase chain reaction and in situ real time fluorescence monitoring, <Analytica Chimica Acta 610 (2008)>, p. 89-96, 2008 Elsevier B.V. All rights reserved, 2008.

* cited by examiner

CONVECTIVE PCR DEVICE

CROSS REFERENCE TO RELATED APPLICATION

This application claims the benefit of priority of Chinese Application number CN201711400272.0, filed on Dec. 22, 2017, which is incorporated herein by reference.

BACKGROUND OF THE INVENTION

1. Field of the Invention

The present invention is related to a PCR convector device, and more particularly, to a device for initiating and performing a polymerase chain reaction by establishing a bottom-up temperature gradient in a reagent container by heating the bottom of the reagent container.

2. Description of the Prior Art

Polymerase chain reaction (hereinafter referred to as "PCR") is a technology for rapid amplification of DNA, and its principle and the main steps include: (a) denature: using a relatively high temperature (90~95 degrees Celsius) for dissociating double-stranded DNA into single stranded DNA, which is then used as a template for replication; (b) primer annealing: when the temperature is lowered to a predetermined level, primers will be adhered to corresponding positions of the target genes; (c) primer extension: when the reaction temperature is about 72 degrees Celsius, by using magnesium ions as enzyme cofactors and DNA polymerase, the deoxy-ribonucleotide triphosphate (dNTP) will sequentially adhere after the primers and extend in accordance with the base sequence of the template, thus synthesizing a DNA fragment.

By repeating the three-step temperature increasing/decreasing process, the number of the target genes can be doubled in each repetition, thus can be $10^9$ times after 40 cycles of the three-step temperature increasing/decreasing process. The signal of the target gene can therefore be greatly amplified. Accordingly, the PCR detection technology is generally used for detecting molecular signals in clinical diagnosis, such as pathogen diagnosis, diagnosis of genetic disease, diagnosis of cancer tumors, or the like. The RT-PCR technique which is derived from PCR also has similar principle and application, and therefore it is widely used in current techniques of clinical diagnosis.

Devices used to perform PCR or RT-PCR reactions often include heat resistant plastics as the materials of the reaction tube. The amplification of nucleic acid is achieved by using the thermostat metal to repeatedly increase and decrease the temperature for the tube so as to reach different temperatures in each three-step temperature increasing/decreasing process. In the current system, the system with thermostat metal requires a relatively larger space, and the entire temperature control system may occupy a larger space and has a large heat capacity ratio. In addition, according to the current practice of operation, it requires 30-35 cycles and about two to three hours for one reaction, making it difficult to reduce the reaction time and hard to apply this technology to those reactions which require to obtain the results in a short time.

In order to improve the problems in the conventional PCR machines, the researchers have developed the PCR and RT-PCR techniques by applying microfluidic chip technology. Microfluidic chips are characterized by adapting various conventional inspecting components, such as a mixing reaction tank, a heating reaction tank, a separation pipe, and a detection tank, etc., into the glass, plastic, or silicon material by etching it to form the reaction tube and analyzing components in the micrometer scale and by applying additional voltage to form a microcurrent, or by using a micropump or centrifugal force, so as to drive the sample's or the reagents' flow between the micro-pipes so as to perform the inspection process. When there is a fluorescent component or a specific probe used in the reagent, the chip can further include a device for detecting the fluorescence to measure the quantity of target gene. Such an integrally molded multi-functional chip is also known as a "lab-on-a-chip." Since all the analysis are carried out in said micropipelines, a very small amount of the reagents and reactants is required for testing, and the analysis time can be relatively shortened due to the high heat transfer efficiency in comparison with the conventional inspection machines. In the current PCR or RT-PCR biochip, it usually includes a micro temperature sensor, a micro-heater and a micro-controller. Since the temperature sensor and the heater are integrated in the PCR or RT-PCR chip, the chip can quickly and more accurately perform the temperature control process, which have three steps: denaturing (around 90~95 degrees Celsius), primer adhering (50~65 degrees Celsius), and template extending (72 degrees Celsius), and the chip can adjust the circle numbers depending on the inspection requirement. The microfluidic chip technology, in comparison with the traditional PCR or RT-PCR technique, is advantageous in that the volume of the microfluidic chip can reduce the overall heat capacity of the reagents or of the reactants, so the reaction time and the reagent consumption can be reduced. However, it is still required for said chip to increase or decrease the temperature in the repeated temperature increasing/decreasing steps, so the time-consuming problem for carrying out these temperature oscillation steps can still not be avoided. So far, a type of micro-chips is developed, which excludes the uses of heaters to execute the repeated temperature increasing/decreasing steps. The chip uses special flow tubes or chambers to make the reactants/reagents repeatedly flow between three temperature zones so as to amplify the target genes. Although the use of such technique in the PCR or RT-PCR process can exclude the time-consuming problem resulted from the repeated heating and cooling processes, such technology requires a complex system such as pressurized fluid systems and liquid driving systems. Because it is hard to predict the volume and the viscosity of the liquid, which is related to the liquid driving system, the system and the instruments with such technology become difficult to design and operate, thus it indirectly limits the development of such technology.

The researchers also develop another technology that uses the thermal convection circulation to perform the PCR or RT-PCR reaction so that the reagent and the reaction product can be in different temperatures at different locations, thereby overcoming the high-capacitance and time-consuming problems in the conventional arts. This technique uses a high-temperature heat source and a low-temperature heat source, and the upper and lower ends of the closed reaction tube which contains reagents and reactants are heated, the liquid can be driven to flow through different temperature regions by the temperature difference between the two ends of the reaction tube, so as to carry out a PCR reaction. This technique overcomes the time-consuming problem caused by the repeated temperature increasing/decreasing steps, and also excludes the external pressurization to drive the liquid flow cycle, however, still needs to avoid the external temperature interference caused by its dual heat source. Therefore, the two heat sources require an individual temperature control system (including a temperature sensor), and the processor should also be able to coordinate the temperatures at the two ends of the reaction tube to give the desired reaction temperature for the primer adhesion. Thus, it requires a very complex mechanism to adjust such temperature. Because most of the heaters are a massive metal, the volume of the machine as well as the heat capacity ratio cannot be reduced, it results in a complex temperature control mechanism and metal heating system and high manufacturing costs. In view of the above problems, there is still a need in the art to develop a polymerase chain reaction apparatus which can solve the above-mentioned problems.

SUMMARY OF THE INVENTION

The present invention is related to a device for the quantitative polymerase chain reaction by thermal convection. The device utilizes a glass coated with a transparent conductive material (or called "a transparent conductive thin film") as a heating unit, wherein a temperature sensor is disposed on the transparent conductive film for detecting the temperature of the heating unit. When starting the device, the bottom of the container with reagents and reactants is brought into contact with the heating unit, so the heat can be transferred from the bottom of the container to the reagent container by the transparent conductive film. Thus, the solution in the bottom of the container adjacent to the contact portion of the film is firstly heated, and the solution located in the portion that is far from the contact portion can be gradually heated by thermal convection. The farther distance from the reagents and reactants to the contact portion, the lower temperature of the container portion can be achieved, and by the continuous thermal convection, the reagents and reactants exhibit a continuous temperature gradient in the reagent container. When the reagents and reactants near the contact portion are heated to 95° C., the reagents and reactants in this portion start a denature step, and then the primer can be annealed and further extended in an appropriate temperature by the thermal convection in the reagent container. By repeating the two processes, PCR can be carried out by this device.

In order to ensure the temperature circle not being affected by the environmental temperature and process the PCR, the reagent container in the present invention has an accommodating space, which can be divided into an upper portion and a lower portion. The upper accommodating portion of the accommodating space can be connected to the external environment, and it contains a tunable fan, a heating coil, and a venting hole, so the temperature of the upper portion can be maintained in a predetermined temperature interval, for processing the reaction successfully. On the other hand, if a device does not contain such upper accommodating space and makes the top of the reagent container exposed to the outer environment, the problem of temperature divergence with respect to the outer environment and the problem of air flowing will occur, causing in the difference of the convection temperature between the reagents and reactants, and resulting in a poor PCR performance. The bottom portion of the accommodating space has an opening for accommodating the reagent container, and there is no other openings connected to the outer environment, thus, after placing the reagent container, the bottom portion of the accommodating space becomes a closed space, and the reagent container positioned in such portion will not be exposed to the outside temperature and the unstable air flow. When the device is under operation, the thermal cycle in the bottom of the reagent container will not be affected by the outside temperature and the unstable air flow. Thus, the reaction for the reagents and reactants in the reagent container can be carried out under a stable temperature cycle.

In other words, in order to eliminate the difference in the external environment temperature caused by the difference of the field, the influence of the thermal cycle efficiency of the device indirectly causes the success or failure of the PCR reaction, and there is sufficient temperature difference to form the internal thermal cycle of the reagent container. Furthermore, the present invention can set a suitable temperature range of the upper and lower portions of the space. The temperature setting of the upper portion of the accommodating space is between 25° C. and 38° C. When the temperature of the upper portion of the accommodating space is higher than the predetermined temperature range, the heat is dissipated through the fan and the venting hole; when the temperature is lower than the predetermined temperature, the heating process is performed through the heating coil to return the temperature of the upper portion of the accommodating space to the predetermined temperature. In the present invention, the temperature of the lower half of the accommodating space is controlled by the temperature setting of the transparent conductive film between 95° C. and 160° C. for the lower portion of the accommodating space.

If the reagent contains a fluorescent dye or a specific probe, the present invention can also include a light source and a light receiver to detect the generated fluorescent light, thereby performing a qualitative, quantitative or semi-quantitative inspection of the reactant. The light source of the present invention can include an LED lamp, a laser lamp, or other light source having a wavelength corresponding to the wavelength of the fluorescent substance or the specific probe, and the applicable photon receiver includes the photodiode, photomultiplier, the charge-coupled device (CCD) or the complementary metal-oxide-semiconductor (CMOS). By using a light source having a specific wavelength, when the PCR product is generated, a fluorescent dye or a specific probe can generate a fluorescent light with the specific wavelength, which is received by the photon receiver, thereto process a qualitative, quantitative or semi-quantitative detection of the PCR product. If the reaction reagent contains two or more than two types of fluorescent dyes or specific probes, the number of the photon receivers and the light sources can be added in order to simultaneously detect two or more kinds of fluorescent signals.

In the present invention, the relative position of the light source and the photon receiver can be adjusted according to different embodiments. If the light source excites the fluorescent dye or the single probe from one side of the reagent container, the photon receiver can be disposed at the bottom, the top or other places of the reagent container which can avoid the interference from the light source to the generated fluorescent signal. Conversely, if the light source is excited by the bottom of the reagent container with the fluorescent dye or the single probe, the photon receiver can be disposed on the side, the top or other places of the reagent container that can exclude the interference from the light source to the generated fluorescent signal. In one preferred embodiment of the present invention, the light source and the photon receiver are respectively located at the bottom of the reagent container and the side of the reagent container, and the relative positions of the two elements are perpendicular or nearly perpendicular to each other. Thus, the received signal is believed to be the fluorescent light generated from the reagent container, instead of the light signal reflected by the reagent container from the light source, thereby ensuring the detection accuracy.

The present invention also includes a temperature control device comprising a transparent conductive film, a temperature sensor, a temperature controller, a conductive foam, and a contact (in the embodiment below, i.e. a thermally conductive patch). The transparent conductive film is not only electrically conductive but also translucent, and is mainly used in two fields of flat panel display and architecture. The transparent conductive film can be mainly divided into a metal film and a metal oxide film, wherein the metal oxide film has excellent conductivity, and can be heated immediately after being connected to the power source, and can be heated to a predetermined temperature in a very short time. The transparent film not only has the advantages of being heated rapidly (comparing to the conventional metal), but also excludes the disadvantage of too large size. At the same time, the transparent conductive film is also highly transparent, making it widely applicable. In general, the transparent conductive material generally including tin oxide, indium oxide, zinc oxide, or indium tin oxide, and the like is also used for coating the glass in the present invention. In addition, if a multi-wavelength light source, such as an LED, is used as a light source at this time, the short-wavelength pass filter material for filtering the non-specific light source may be utilized (spraying, vapor deposition, sputtering, etc.) on the other side which is coated with the transparent conductive material. The light of the light source that cannot excite the fluorescent substance or the specific probe is filtered out, and only the light of the light source that can excite the fluorescent substance or the specific probe is allowed to pass through the transparent conductive film and the reagent container and excite the fluorescent substance or the specific probe therein. As such, the optical signal measured by the photon receiver can be ensured to be the fluorescent signal of the PCR product.

In the present invention, when the reagent container containing the reagents and reactants is in contact with the heated transparent conductive film, the solvent in the contact portion starts to heat up, and is thermally circulated in the reagent container by heat convection. When the temperature of the transparent conductive film has reached the predetermined value, the temperature sensor will detect this condition and reduce or maintain the heat source output of the heater so that the transparent conductive film will not continue to heat up and maintain the proper reaction temperature. When the temperature of the transparent conductive film is already lower than the predetermined temperature, the temperature sensor will increase the heat source output of the heater, and raise the transparent conductive film to the predetermined temperature to facilitate the smooth reaction of the PCR reaction. When the PCR in the reagent container begins to process, the light of the light source can also pass through the transparent conductive film to excite the product to generate fluorescence which will be detected by the photon receiver. In addition, the contact nodes are applied to the current delivered by the power supply, and the contact nodes are located on the same side as the transparent conductive film.

The invention comprises a light source control device for activating or deactivating the light source for the excitation of fluorescent. The present invention also includes one or more processors for coordinating the processing of the temperature control device and the light source control device. The processor can also be configured to receive one or more types of fluorescent signals transmitted from the photon receiver and analyze the strength and type of the signal by a built-in program in the processor. The program operation can output the concentration of one or more target genes, or shows if the target gene is present in the reactants or not.

The device disclosed by the invention utilizes a transparent conductive film instead of a conventional heater to reduce the size of the whole device, and achieves the PCR reaction temperature by means of liquid heat convection in the reagent container, thereby eliminating the process of repeatedly heating and lowering the heater, saving the overall reaction time. By utilizing the upper and lower accommodating spaces for exhibiting temperature regulation process, the qualitative and quantitative effects of the target gene can therefore be achieved in a short time.

In order to achieve the foregoing objects, a preferred embodiment is provided in accordance with the present invention.

These and other objectives of the present invention will no doubt become obvious to those of ordinary skill in the art after reading the following detailed description of the preferred embodiment that is illustrated in the various figures and drawings.

DETAILED DESCRIPTION

In the following context, the description, in combination with the figures, will explain the structure and the effect of the preferred embodiment in the present invention. In addition, the terms "before", "after", "right", "left", "up", "down" are used to describe the positions of the structures or the components, so as to correspond the space relationship when the user operates the preferred embodiment of the present invention.

Figure 1:
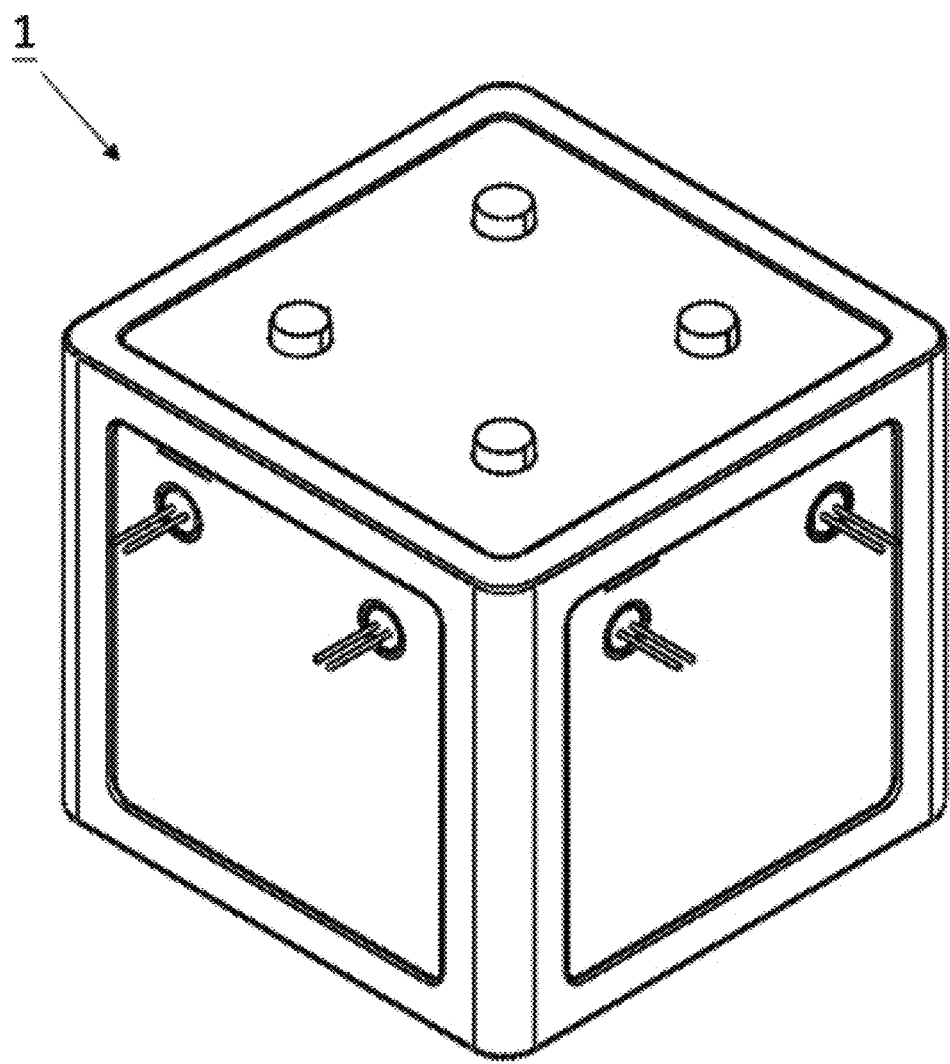
FIG. 1 is an external view of the device of the present invention.
Figure 2:
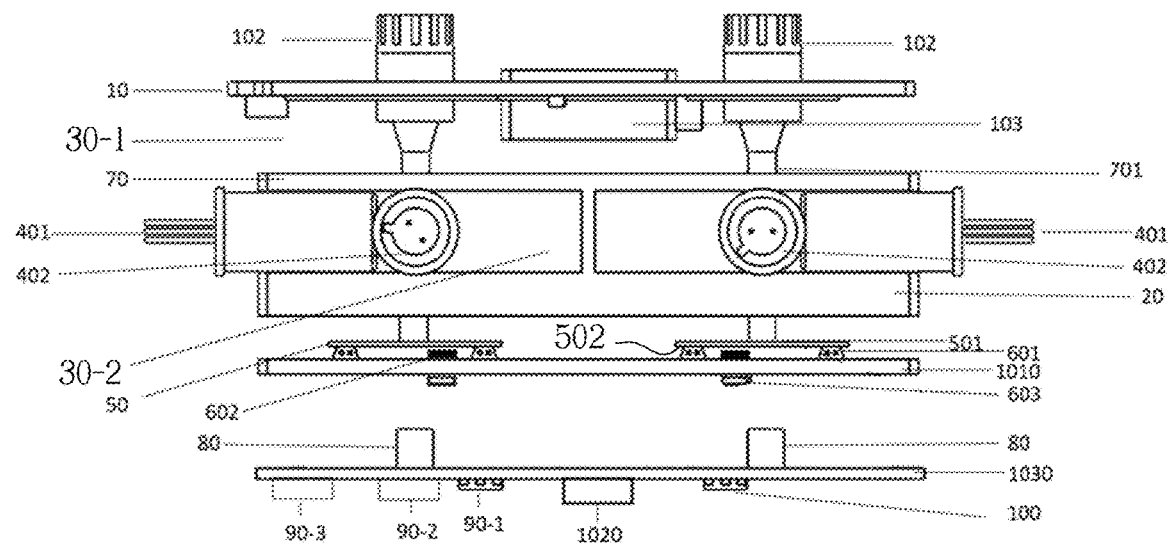
FIG. 2 is a schematic view showing the relative positions of the frame, the perforation and the reagent container of the present invention.
Figure 3:
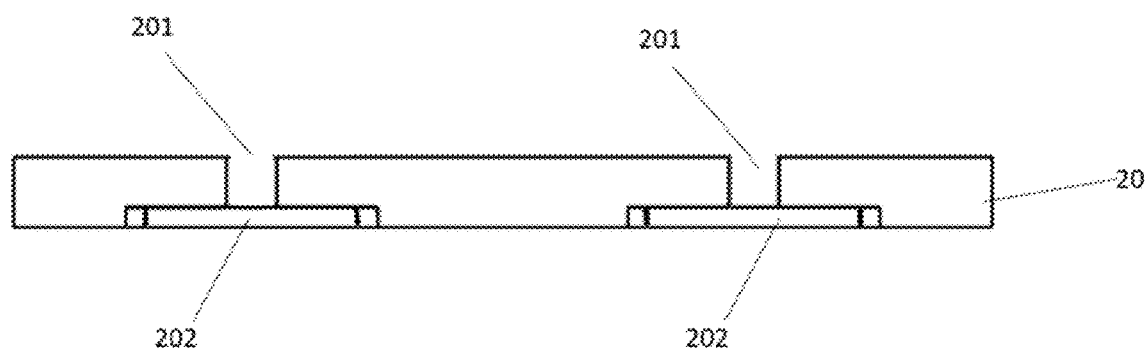
FIG. 3 is a schematic cross-sectional side view of the clamping space of the present invention.
Figure 4:
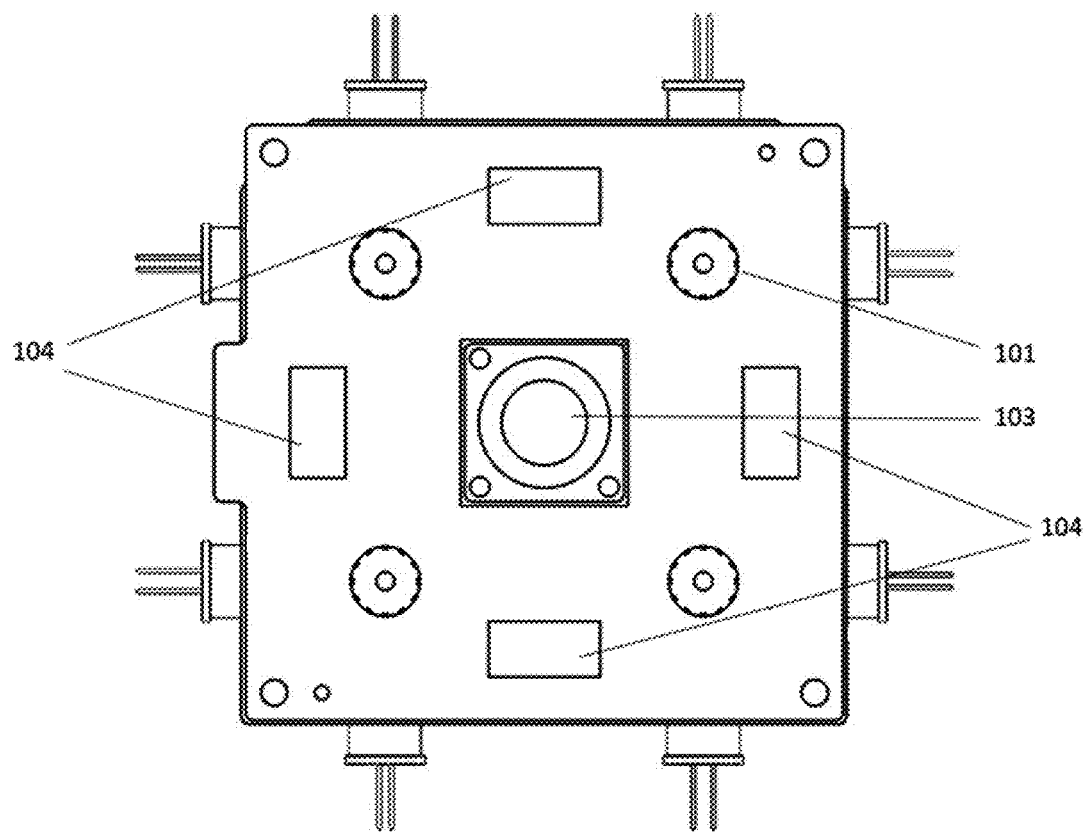
FIG. 4 is a schematic diagram showing the first upper surface of the first frame in the device.
Figure 5:
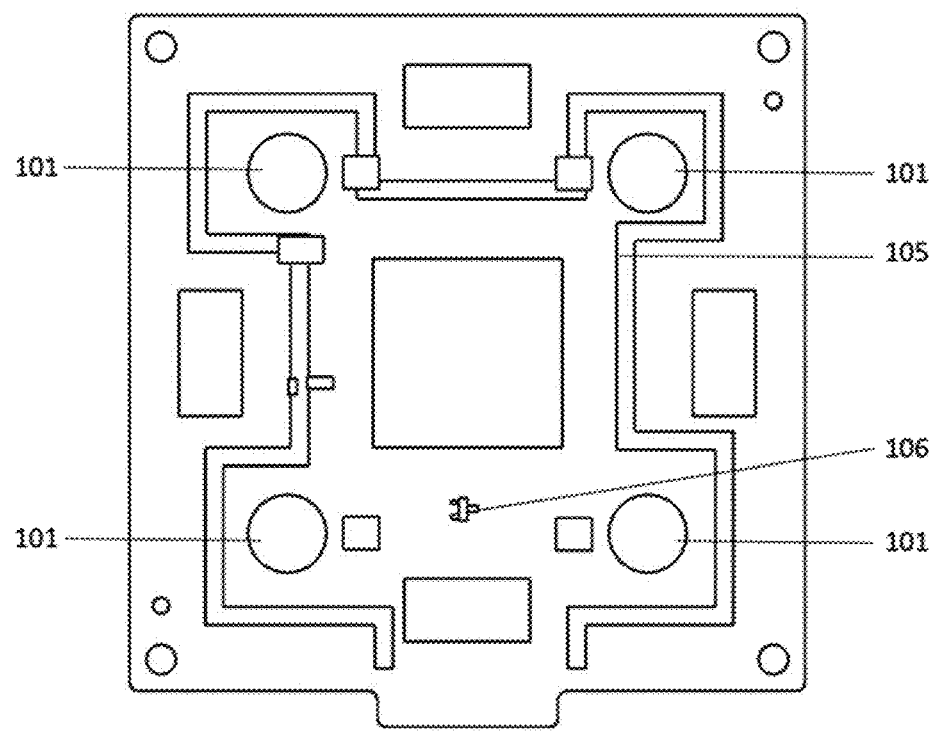
FIG. 5 is a schematic diagram showing the first lower surface of the first frame in the device.

Please refer to FIG. 1, which shows an assembled appearance of a thermal convection polymerase chain reaction device (1) according to one preferred embodiment of the present invention. Referring to FIG. 2, FIG. 3, and FIG. 4, the device (1) according to one preferred embodiment of the present invention includes a first frame (10), a second frame (20), a third frame (70), a fourth frame (1010), a bottom plate (1030), an upper accommodating space (30-1), and a lower accommodating space (30-2). The first frame (10) has a first perforation hole (101), a fan (103), and a venting hole (104), wherein the first perforation hole (101) can be inserted with a test tube (102) containing the reagents and reactants. Referring to FIG. 5, the lower surface of the first frame (10) includes a heating coil (105) and a first temperature sensor (106), and the first temperature sensor (106) is used to measure the temperature of the upper accommodating space (30-1). The heating coil (105) is used for receiving signals and heating to increase the temperature of the upper accommodating space. Conversely, the fan (103) and the four venting holes (104) are used for heat dissipation to lower the temperature of the upper accommodating space.

Referring to FIG. 2 and FIG. 3, the second frame (20) has a second perforation hole (201) and a clamping groove (202), wherein the second perforation hole (201) can be inserted with the test tube (102), the test tube (102) can be fixed above the clamping groove (202), and the clamping groove (202) can accommodate a transparent conductive film (502). The side of the transparent conductive film (502) that is not in contact with the test tube (102) includes a thermal conductive patch (602). The third frame (70) is located between the first frame (10) and the second frame (20), and is approximately parallel to the first frame (10) and the second frame (20). The third frame (70) includes a third perforation hole (701). An upper accommodating space (30-1) having no internal compartment is disposed between the first frame (10) and the third frame (70), and a lower accommodating space (30-2) having internal compartments is disposed between the third frame (70) and the second frame (20), wherein the lower accommodating space (30-2) is internally divided by several sheets to form the internal compartments, and the amount of the internal compartments is equal to the amount of the entire test tubes (102) that can be placed at one time in the device. In addition, the number of the first perforation holes (101), the second perforation holes (201), and the third perforation holes (701) is also the same as the number of test tubes (102) that can be placed at one time in the device.

When being placed, the test tube (102) sequentially passes through the first perforation hole (101), the third perforation hole (701), and the second perforation (201), and the end of the test tube (102) is fixed to and in contact with the transparent conductive film (502). In this situation, the upper accommodating space (30-1) becomes a half-open space, and the lower accommodating space (30-2) becomes a closed space, so the test tube (102) placed therein will not be exposed to the air.

Referring to FIG. 2, in this embodiment, the photon receiver is a photodiode, and the embodiment includes two sets of photodiodes (401) (402), which can respectively detect different wavelengths of fluorescence. The two sets of photodiodes (401) (402) are respectively located at sidewalls of the test tube (102) and are approximately perpendicular to the test tube (102), which is to ensure that the received photoelectric signal is not reflected by the test tube (102).

Referring to FIG. 2, the present invention further includes a fourth frame (1010), a power supply (1020), a bottom plate (1030), a light source (80), a light source controller (90-1), a first temperature controller (90-2), a second temperature controller (90-3), a processor (100), and a glass device (50) comprised of a glass and a contact node. In this embodiment, the contact node is a thermal conductive patch (602). The fourth frame (1010) is approximately parallel to the second frame (20) and is in contact with the transparent conductive film (502) through the conductive foam (601) that is fixed on the fourth frame (1010). The upper surface of the glass device (50), that is, the side being in contact with the test tube (102), is coated with a short-wavelength filter material for filtering non-specific wavelengths from the light source (80), enhancing the excitation of the fluorescent substance or the efficiency of the specific probe. The lower surface of the glass device (50) includes a transparent conductive film (502), which is formed by coating indium tin oxide on one side of the transparent glass. In addition, the shape and volume of the glass device (50) is approximately equivalent to the clamping groove (202) that can accommodate the glass device (50).

The conductive foam (601) is fixed on the fourth frame (1010) near the clamping groove (202), and when the device (1) starts to operate, the fourth frame (1010) and the second frame (20) are closely adjacent to each other. The conductive foam (601) is used to transfer the received electrical energy to the transparent conductive film (502) to start heating the transparent conductive film (502). The side of the fourth frame (1010) that is not in contact with the transparent conductive film (502) includes a second temperature sensor (603) for sensing the temperature of the transparent conductive film (502). The thermal conductive patch (602) is configured to conduct heat energy on the transparent conductive film (502) to the second temperature sensor (603) when the transparent conductive film (502) is initially heated, so that the second temperature sensor (603) can measure the temperature of the transparent conductive film (502).

The bottom plate (1030) is configured to provide a light source (80), a light source controller (90-1), a first temperature controller (90-2), a second temperature controller (90-3), a processor (100), and a power source (1020) for fixing on it. The light source (80) is used to provide light required to excite the fluorescent substance or the specific probe. In the present embodiment, the LED light is used as the excitation light source (80), and the switch on/off and illumination is regulated by the light source controller (90-1). The power supply (1020) and the processor (100) are also fixed on the bottom plate (1030), and the processor (100) is configured to receive the signal from the light source controller (90-1), that is, the signal from the first temperature sensor (106) and the second temperature sensor (603), and the signal is then analyzed and outputted to the first temperature controller (90-2) and the second temperature controller (90-3) to control the temperature. Meanwhile, the processor (100) can also receive the signal measured by the two sets of photodiodes (401) (402), analyze it and give the power supply (1020) its required power for the device (1).

When the device (1) starts to operate, the test tube (102) containing the reagents and reactants is placed in the first perforation hole (101) of the first frame (10), sequentially passing through the third perforation hole (701) of the third frame (70), the second perforation hole (201) of the second frame (20), and the bottom of the test tube (102) is in contact with the upper surface (501) of the glass device (50). At this time, the top of the liquid level in the test tube (102) is approximately level to the top of the lower accommodating space (30-2), so that the lower accommodating space (30-2) becomes an enclosed space, the upper accommodating space (30-1) becomes a half open space. The first temperature sensor (106) begins to measure the temperature of the upper accommodating space (30-1) and reports it back to the processor (100) for monitoring the ambient temperature.

The power supply (1020) transmits current to the transparent conductive film (502) through the conductive foam (601) and starts to heat the transparent conductive film (502), wherein the temperature of the transparent conductive film (502) is measured and transferred to the second temperature senor sensor (603) by the thermal conductive patch (602), and the measured temperature is then transferred to the processor (100). In this embodiment, when the reaction is performed, the heating temperature of the transparent conductive film (502) is set at 125° C. Therefore, if the temperature measured by the second temperature sensor (603) is lower than the set temperature, the processor (100) will control the second temperature controller (90-3) to raise the temperature. When the temperature of the transparent conductive film (502) is raised to the predetermined temperature, the processor (100) stops heating. Conversely, if the temperature measured by the second temperature sensor (603) is higher than the predetermined temperature, the processor (100) will drive the second temperature controller (90-3) to start cooling. When the temperature of the transparent conductive film (502) is lowered to the set temperature, the processor (100) stops cooling.

After the transparent conductive film (502) starts to be heated, the bottom of the test tube (102) is brought into contact with the upper surface (501) of the glass device (50), the reagents and reactants at the bottom of the test tube (102) are heated by a thermal convection. After heating for a period of time, the reagents and reactants in the test tube (102) are also heated to form a thermal convection cycle. Since the level of the reagents and reactants in the test tube (102) are approximately the same as the height of the lower accommodating space (30-2), and the lower accommodating space (30-2) is a completely closed space after the test tube (102) is placed in the device (1), the thermal convection cycle inside the test tube (102) is not affected by external temperature.

The portion of the test tube (102) located in the upper accommodating space (30-1) is also heated by the thermal convection from the reactants and reagents in the test tube (102), thereby increasing the temperature of the air near the upper accommodating space (30-1). At this time, the first temperature sensor (106) detects the temperature of the upper accommodating space (30-1), and then transfers the detected result to the processor (100). In the present embodiment, the temperature of the upper accommodating space (30-1) is preferably maintained at 28° C. Therefore, when the temperature measured by the first temperature sensor (106) is lower than the set temperature, the processor (100) will inform the first temperature controller (90-2) to trigger the heating coil (105) to raise the temperature; when the temperature of the upper accommodating space (30-1) is raised to an acceptable interval, the processor (100) then stop the heating of the coil (105). Conversely, if the temperature measured by the first temperature sensor (106) is higher than the set temperature, the processor (100) notifies the first temperature controller (90-2) to decrease the temperature, and simultaneously starts the fan (103) for dissipating heat through the venting hole (104); when the temperature is lowered to an acceptable temperature, the processor (100) then stops the fan (103).

When the thermal convection cycle in the test tube (102) reaches the three reaction temperatures required for PCR, the PCR reaction begins. When the PCR reaction begins, the light source controller (90-1) on the bottom plate (1030) then turns on the light source (80), and the light from the light source (80) can pass through the transparent conductive film (502). Light with non-specific bandwidth is filtered by the short-wavelength filter material on the upper surface (501) of the glass device (50), leaving only the specific bandwidth source (80) to pass through the short-wavelength filter material and exciting two different specific probes pre-filled in the test tube (102). After the fluorescence is generated, the optical signal is respectively detected by the first photodiode (401) and the second photodiode (402), and the detected signal is then transmitted to the processor (100) for data analysis. When the PCR reaction is over, the processor (100) coordinates the light source controller (90-1) to turn off the light source (80), and also coordinates the power supply (1020) to stop supplying power to the thermal conductive patch (602). The transparent conductive film (502) will not continue to heat up, and the processor (100) will analyze all the signals received from the first photodiode (401) and second photodiode (402) and output the analysis results.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A device for quantitative polymerase chain reaction by thermal convection throughout a reagent container, wherein the reagent container is loaded with a reactant and a reagent, in which the reagent comprises a fluorescent dye or a probe, wherein the device comprises:
   a first frame including a first upper surface, a first lower surface opposite to the first upper surface, a first perforation hole, a fan, and a venting hole, wherein a heating coil and a first temperature sensor are disposed on the first lower surface;
   a second frame disposed under the first frame and including a second upper surface, a second lower surface opposite to the second upper surface, a second perforation hole, and a clamping groove wherein the clamping groove is disposed on the second lower surface and connected to the second perforation hole, and an accommodating space is formed between the first frame and the second frame for accommodating the reagent container;
   a glass device disposed in the clamping groove and including a glass upper surface, a glass lower surface opposite to the glass upper surface, and a contact node, wherein a transparent conductive film is disposed on the glass upper surface or the glass lower surface, a size of the glass device is the same as that of the clamping groove, the glass device is fixed to the clamping groove via the glass upper surface or the glass lower surface, and the contact node is disposed at the same side of the glass device coated with the transparent conductive film;
   a third frame disposed between the first frame and the second frame and including a third perforation hole, wherein the accommodating space is divided by the third frame into an upper accommodating space between the first frame and the third frame to enable a top portion of the reagent container to be exposed to the upper accommodating space, and a lower accommodating space between the third frame and the second frame to enable a bottom portion of the reagent container to be exposed to the lower accommodating space, the upper accommodating space is a space to connect to an external environment via the venting hole, the lower accommodating space is an enclosed space, the upper accommodating space is free from communicating to the lower accommodating space upon the reagent container passing across the third perforation hole, and the fan, the heating coil, and the venting hole are disposed within the upper accommodating space, and the transparent conductive film is disposed within the lower accommodating space;
   a power supply device for supplying power to the contact node to heat the glass device;
   a light source for exciting the fluorescent dye or the probe;
   a photon receiver for detecting and receiving fluorescent signals; and
   a processor for processing and regulating the device;

wherein the reagent container passes across the first perforation hole of the first frame, the third perforation hole of the third frame, and the second perforation hole of the second frame sequentially from top to bottom, with the top portion of the reagent container being disposed within the upper accommodating space without communicating with the lower accommodating space, and with the bottom portion of the reagent container being disposed within the lower accommodating space to contact the glass upper surface, wherein the power supply device supplies a current to the contact node to start to heat the glass device, and when the glass device is heated to a predetermined temperature, the polymerase chain reaction starts, and the fluorescent dye or the probe is excited by the light source, and the fluorescent dye or the probe emits a light with a specific wavelength, which is measured by the photon receiver, and the result is fed back to the processor, wherein if a temperature of the upper accommodating space measured by the first temperature sensor is higher than a predetermined temperature range, the measured temperature will be fed back to the processor, the processor then turns on the fan to lower the temperature, until the measured temperature is cooled to a predetermined environmental range, the result of the first temperature sensor will be fed back to the processor, which then stops the fan; if the temperature of the upper accommodating space measured by the first temperature sensor is lower than the predetermined temperature range, the measured temperature will be fed back to the processor, the processor then turns on the heating coil to increase the temperature, until the measured temperature is heated to the predetermined environmental range, the result of the first temperature sensor will be fed back to the processor, which then stops the heating coil.

2. The device according to claim 1, wherein the device is applied to a real-time quantitative polymerase chain reaction.

3. The device according to claim 1, wherein the photon receiver is a photodiode, a photomultiplier, a charge-coupled element (CCD), or a complementary metal oxide semiconductor (CMOS).

4. The device according to claim 1, wherein the light source is an LED or a laser.

5. The device according to claim 1, wherein the photon receiver is at a substantially perpendicular angle to the light source.

6. The device according to claim 1, further comprising a second temperature sensor for sensing a temperature of the glass device and feeding back the temperature to the processor.

7. The device according to claim 5, wherein when the light source is vertically below the second perforation hole; and the photon receiver is located in the lower accommodating space and is perpendicular to the light source.

8. The device according to claim 5, wherein when the light source is located in the lower accommodating space; and the photon receiver is located below the second perforation hole and is perpendicular to the light source.

9. The device according to claim 1, wherein the transparent conductive film comprises tin oxide, indium oxide, zinc oxide, or indium tin oxide.

10. The device according to claim 9, wherein an opposing side with respect to the transparent conductive film of the glass device is coated with a short-wavelength filter for filtering a non-specific light source.

11. The device according to claim 1, wherein the contact node is a heat conductive patch.

12. The device according to claim 1, wherein the third frame is parallel to the first frame and the second frame.

13. The device according to claim 1, wherein the predetermined environmental range is between 25 degrees Celsius and 38 degrees Celsius, and when the power supply provides current to the contact node for starting to heat the glass device, the predetermined temperature range is between 90 degrees Celsius and 160 degrees Celsius.

14. A device for quantitative polymerase chain reaction throughout a reagent container, wherein the reagent container contains a fluorescent dye or a probe, the device comprising:

a first frame, a second frame, and a third frame parallelly disposed with each other to define an upper accommodating space between the first frame and the third frame to enable a top portion of the reagent container to be exposed to the upper accommodating space, and a lower accommodating space between the third frame and the second frame to enable a bottom portion of the reagent container to be exposed to the lower accommodating space;

a fan and a heating coil disposed on the first frame individually and within the upper accommodating space;

a glass device, disposed on the second frame, within the lower accommodating space and directly contacting the bottom portion of the reagent container, wherein the glass device includes a glass and a contact node disposed on a side of the glass coated with a transparent conductive film;

a light source, disposed under the transparent conductive film for exciting the fluorescent dye or the probe;

a power supply device, disposed under the second frame for supplying power to the contact node to heat the glass device;

a photon receiver disposed on sidewalls of the reagent container for detecting and receiving fluorescent signals; and a processor, disposed under the second frame for processing and regulating the device;

wherein the upper accommodating space connects to an external environment through a venting hole disposed on the first frame and is free from communicating to the lower accommodating space upon the reagent container penetrating the first frame, the third frame and the second frame sequentially, and the lower accommodating space is an enclosed space thereupon, wherein the bottom portion of the reagent container is free from contacting the upper accommodating space after inserting the reagent container into the lower accommodating space, and the top portion of the reagent container is free from contacting the lower accommodating space after inserting the reagent container into the device.

* * * * *